(12) United States Patent
Bertocchio

(10) Patent No.: US 6,866,787 B1
(45) Date of Patent: Mar. 15, 2005

(54) PROCESS FOR DRYING DIFLUOROMETHANE

(75) Inventor: Rene Bertocchio, Vourles Par Vernaison (FR)

(73) Assignee: Arkema, Paris la Defense (FR)

( * ) Notice: Subject to any disclaimer, the term of this patent is extended or adjusted under 35 U.S.C. 154(b) by 0 days.

(21) Appl. No.: 09/456,558

(22) Filed: Dec. 8, 1999

(30) Foreign Application Priority Data

Dec. 8, 1998 (FR) .............................. 98 15469

(51) Int. Cl.[7] ..................... B01D 15/00; B01D 53/04; B01D 53/26
(52) U.S. Cl. .................... 210/673; 95/123; 210/689
(58) Field of Search ................... 95/117, 120, 121, 95/122, 123; 62/85, 475; 210/673, 689; 570/179

(56) References Cited

U.S. PATENT DOCUMENTS 4,663,052 A * 5/1987 Sherman et al. ............ 210/689
5,347,822 A * 9/1994 Lavin et al. ................ 210/689
5,574,214 A * 11/1996 Balton et al. ............... 210/689
5,897,686 A * 4/1999 Golden et al. ................ 95/120
6,020,281 A * 2/2000 Lavin et al. .................. 502/64

FOREIGN PATENT DOCUMENTS

| DE | 209 182 | 7/1982 |
| FR | 2 657 870 | 2/1990 |
| JP | 8-173799 | 2/1995 |
| JP | 8 173799 A | 7/1996 |
| WO | WO 91/15445 | 3/1991 |

OTHER PUBLICATIONS

French Search Report.

* cited by examiner

Primary Examiner—Ivars C. Cintins
(74) Attorney, Agent, or Firm—Jones Day

(57) ABSTRACT

Process for drying wet F32, which comprises placing a stream of the said F32 in continuous contact with a feed stock of a composition comprising a molecular sieve chosen from a 3A type sieve, at a temperature of between 5 and 78° C. and at a pressure of between 0.5 and 25 atm.

13 Claims, 1 Drawing Sheet

PROCESS FOR DRYING DIFLUOROMETHANE

FIELD OF THE INVENTION

The present invention relates to the field of fluorohydrocarbons and its subject is, more particularly, a process for the continuous drying of wet difluoromethane ($CH_2F_2$), using a molecular sieve, of A type, and which can be used in an industrial production plant.

BACKGROUND OF THE INVENTION

Difluoromethane (known in the art by the abbreviation F32 or HFC-32) is one of the possible replacements for chlorofluorocarbons (CFC) with which the Montreal Protocol is concerned. It is more particularly intended to replace chloropentafluoroethane (F115, whose action on ozone is accompanied by a very strong contribution towards the greenhouse effect) and, in the near future, F22 or chlorodifluoromethane. In this respect, it forms part of the composition of several mixtures of quasi-azeotropic nature, such as R407 C (mixture with HFC-125 or pentafluoroethane in a proportion of 50%/50% by weight) or R410 A (HFC-32/HFC-125 or pentafluoroethane/HFC-134a or 1,1,1,2-tetrafluoroethane mixture in a proportion of 23%/25%/52% by weight), which are used in the refrigeration industry.

F32 can be obtained by fluorination of methylene chloride ($CH_2Cl_2$) using hydrogen fluoride (HF) in the presence of a catalyst, or by hydrogenolysis of dichlorodifluoromethane (F12) or chlorodifluoromethane (F22), or alternatively by decomposition, in the presence of HF, of a-fluoro ethers under the action of Lewis acids.

Some of these processes require acidic or basic washes which introduce larger or smaller amounts of water into the final product. This product must thus undergo an additional drying operation in order to satisfy the specifications normally set for hydrofluorocarbons (HFCs), i.e. less than 10 ppm water. Such a specification is required in order to avoid problems of corrosion in refrigeration machines.

Molecular sieves, also known as synthetic zeolites, are chemical compounds widely used in the industry as adsorbing agents, in particular for drying gases or liquids. There are metallic aluminosilicates with a three-dimensional crystal structure consisting of an assembly of tetrahedra. These tetrahedra are formed by four oxygen atoms which occupy the peaks, and which surround either a silicon atom or an aluminium atom placed at the centre. These structures generally contain cations to make the system electrically neutral, such as those derived from sodium, potassium or calcium.

In the case of molecular sieves, of the so-called A type, the tetrahedra are assembled such that they compose a truncated octahedron. These octahedra are themselves arranged in a simple cubic crystal structure, forming a network with cavities approximately 11.5 Å in diameter. These cavities are accessible via apertures, or pores, which can be partially blocked by means of cations. When these cations are derived from sodium, these cavities have an aperture diameter of 4.1 Å, and this thus gives a so-called 4 A molecular sieve. The crystal structure of such a sieve can be represented by the following chemical formula:

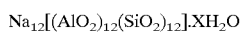

$Na_{12}[(AlO_2)_{12}(SiO_2)_{12}].XH_2O$ in which X, which represents the number of molecules of water forming part of the structure (water of crystallization), can be up to 27, which represents 28.5% by weight of the anhydrous zeolite.

After removal of the water of crystallization by heating to a temperature of about 500 to 700° C., the cavities in these substances are available for the selective adsorption of various gases or liquids. Thus, the pores in the various types of zeolite allow passage and adsorption, in the corresponding cavities, only of molecules whose effective diameter is less than or equal to the effective diameter of the pores. In the case of the drying of gases or liquids, it is thus water molecules which are retained by selective adsorption inside the abovementioned cavities, while the substance to be dried is itself not or only negligibly adsorbed.

The size of the apertures (or pores) can, moreover, be modified according to the different types of molecular sieve. Thus, by exchanging most of the sodium ions of a 4A molecular sieve for potassium ions, the 3A molecular sieve is obtained, the pores of which have a diameter of about 3 Å. The 5A molecular sieve is prepared by replacing the sodium ions with calcium ions, the effective diameter of the pores then being about 5 Å.

Sieves of 3A, 4A or 5A type are widely commercially available.

In practical terms, the molecular sieves can be combined with other substances such as binders, in particular clays, and the compositions obtained are shaped, for example, into granules, beads or extrudates.

The molecular sieves thus conditioned are used industrially by loading into drying columns, into which the wet gas is introduced, and from which it emerges dried.

After a certain period of running in a drying column, which varies with the operating conditions (flow rate of gas to be dried, amount of molecular sieve), an increase in the water content of the dried gas leaving the column is observed. This moment corresponds to the obtainment of the water-saturation capacity of the sieve feed stock, i.e. the maximum amount of water which can be adsorbed. This amount is generally about 20% by weight, expressed relative to the weight of dry sieve.

The sieve feed stock thus saturated with water must then be subjected to a so-called regeneration treatment, after which the initial capacity of the sieve to adsorb water is restored. This treatment usually consists in passing a stream of an inert gas, at a temperature of between 200° C. and 300° C., into the column. In practical terms, this treatment of the saturated sieve feed stock is carried out in the same column as that in which the stream of gas to be dried was introduced. The same drying column thus functions occasionally in a phase of drying the wet gas, and occasionally in a phase of regenerating the molecular sieve feed stock with the inert gas. However, after a certain number of these drying-regeneration cycles, an irreversible decrease in the water-saturation capacity of the sieve feed stock is observed, and it is then necessary to stop running the column so as to renew the sieve feed stock with a fresh feed stock.

In the present text, the expression "fresh sieve feed stock" means a sieve feed stock which has not been used as a drying agent.

Under the conditions of the industrial practice of drying gases using molecular sieves, 2 drying columns are usually used, which can run alternately, one being in the drying phase while the other is in the regenerating phase.

The drying of F32 with molecular sieves poses a specific problem on account of the proximity of effective diameter between the molecules of F32 and of water (0.33 nm and 0.21 nm respectively).

Thus, patent application FR 2,705,586 clearly mentions the placing in contact, in a pressurized container, of wet F32 with a 3A type molecular sieve and an ester oil at a temperature of 120° C.

However, that document teaches that, under these conditions, the F32 is adsorbed onto the said sieve and undergoes a decomposition reaction, the effect of which is, via a modification of the sieve's crystal state, to greatly reduce its water-saturation capacity.

That document concludes that such a sieve is not suitable for use as an agent for drying F32. The patent application consequently recommends, with the aim of drying F32 circulating as a refrigerant inside a refrigeration machine, a molecular sieve obtained by a complementary treatment of a 3A type sieve which results in a decrease in the size of the pores.

DETAILED DESCRIPTION OF THE INVENTION

Figure 1:
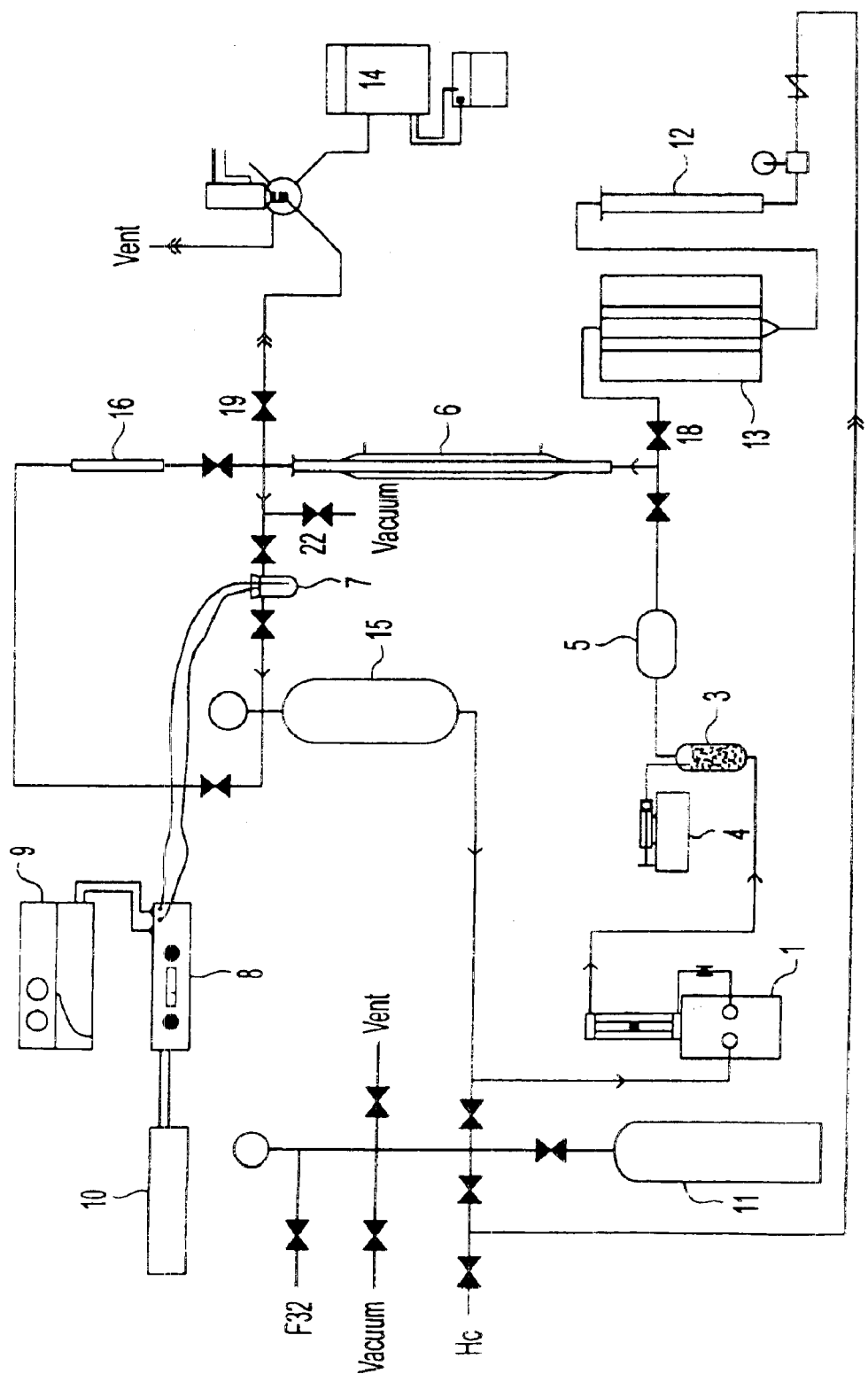
FIG. 1 is a diagram which depicts an arrangement of devices for conducting a process of the present invention.

It has now been found that this drawback can be avoided by drying a stream of F32 produced continuously, within a specific temperature range, and by carrying out, in particular, a specific process for regenerating the sieve feed stock.

One aim of the present invention is thus to propose a process for drying wet F32, using a simple, commercially available molecular sieve which can be used in a plant for the industrial production of F32.

Another aim of the invention is to propose a process for continuously drying wet F32 which results in selectively separating the water from the F32, with reduced losses of F32.

Another aim of the invention is to propose a process for continuously drying wet F32, which comprises a step for regenerating the molecular sieve feed stock which keeps its water-saturation capacity more or less constant.

Another aim of the invention is to propose a process for continuously drying wet F32, which allows a reduction in the time for which the drying columns are stopped in order to renew the molecular sieve feed stock.

It has now been found that the above-mentioned aims are achieved, partially or totally, by means of the process according to the invention which is described below.

The present invention thus relates to a process for drying wet F32, which comprises placing a stream of the said F32 in continuous contact with a feed stock of a composition comprising a molecular sieve chosen from a 3A, 4A or 5A type sieve, at a temperature of between 5 and 78° C., preferably at room temperature, and at a pressure of between 0.6 and 25 atm, preferably between 0.6 and 17 atm.

In contrast with the teaching of the prior art, it is thus possible, in accordance with the invention, to use A type sieves, which are commercially available to dry F32 continuously.

The stream of F32 to be dried can be a stream of gas or liquid. When the stream of F32 to be dried is liquid, the process is advantageously performed at a pressure of between 9 and 25 atm, preferably between 12 and 17 atm.

When, according to a preferred variant, the stream of F32 to be dried is a gas, the process is performed at a pressure of between 0.6 and 10 atm, preferably between 0.8 and 5 atm.

The stream of F32 to be dried generally comprises a water content of less than 10,000 ppm, preferably less than 6000 ppm.

The wet F32 is preferably placed in contact with the sieve feed stock in a drying column located in the downstream part of a plant for manufacturing F32.

Before using it for drying the stream of F32, the fresh molecular sieve feed stock is subjected to an activation treatment. The aim of this treatment is to remove the water adsorbed after the manufacture of the material during its storage and the manipulations preceding its installation in the drying column. This treatment generally comprises heating to a temperature of between 200 and 300° C. and at a pressure in the region of atmospheric pressure.

The flow rate of the stream of F32 to be dried and the amount of sieve feed stock suited to the drying operation can be determined without excessive difficulty by a person skilled in the art who is competent in chemical engineering, by means of calculation and tests, as a function of the size of the industrial plant.

According to a preferred variant of the process according to the invention, the molecular sieve used is a 3A type sieve. On account of its effective pore diameter, such a sieve advantageously has a reduced capacity for adsorbing F32 and improved efficacy.

According to a preferred variant of the process according to the invention, the molecular sieve feed stock used is advantageously regenerated (after it has reached its water-saturation capacity) by the process which consists in heating the said feed stock to a temperature of between 120° C. and 300° C., preferably between 150° C. and 250° C., at an absolute pressure of less than 100 mm Hg, preferably less than 80 mm Hg. The duration of this process is advantageously determined so as to desorb virtually all of the amount of products (essentially the water and, to a minor amount, the residual F32) which are adsorbed after drying the wet F32. This amount is denoted by the term "initial amount" in the lines hereinbelow.

According to another preferred variant of the process according to the invention, the molecular sieve feed stock used is regenerated by the process which consists in passing a stream of an inert gas, such as helium, over the said feed stock, at a pressure in the region of atmospheric pressure, by working firstly:

(i) at a temperature at least between 70° C. and 170° C., preferably between 80° C. and 165° C., for the time required to remove at least 80%, preferably at least 90%, of the initial amount of F32 adsorbed in the feed stock, and then (ii) at another temperature of between 180° C. and 300° C., preferably between 190° C. and 250° C., for the time required to remove at least 90%, preferably at least 95%, of the initial amount of water adsorbed in the feed stock.

The running time required at the temperature (i) is determined by monitoring the profile of the content of F32 in the inert gas, leaving the regeneration column, by suitable control methods, such as by chromatographic assay. The running time required at the temperature (ii) is determined in a similar manner, for example using a humidity meter. These times are based on a certain number of parameters which depend on the plant and which are-well known to those skilled in the art: flow rate of the inert flushing gas, heat of desorption of the water and of the F32, calorific mass of the sieve and of the metallic apparatus containing the sieve.

These last 2 embodiments of the process according to the invention, relating to the methods for regenerating the sieve feed stock, are particularly advantageous since they make it possible, after the regeneration, to keep the water-saturation capacity of the molecular sieve feed stock at a value which is more or less equal to that before regeneration. Thus, the same sieve feed stock used industrially can be used effectively in a larger number of cycles: drying of F32/regeneration. Among these two variants, the one using a stream of inert gas is more particularly preferred since it is simpler to implement and run in an industrial plant.

When the treatment to regenerate the molecular sieve feed stock is carried out by means of the 2-step process which has just been described, it is particularly advantageous to carry out step (i) by first working:

(i1) at a first temperature of between 70° C. and 130° C., preferably between 100° C. and 125° C., for the time required to remove at least 60% (preferably at least 70%) of the initial amount of F32 adsorbed, and then (i2) at a second temperature of between 130° C. and 170° C., preferably between 145° C. and 165° C., or the time required to remove at least 80%, preferably at least 90%, of the initial amount of F32 adsorbed.

Such a treatment allows even better maintenance of the water-saturation capacity of the sieve feed stock. It also allows recovery of F32 whose water content is considerably lower than that of the wet F32 to be dried, in particular after step (i1).

The regeneration treatment for the sieve feed stock, in accordance with one of the two variants described above, is advantageously carried out in the same column as that mentioned above. Even more advantageously, the drying process according to the invention is carried out in two columns in parallel, one running in the phase for drying the actual wet F32, the other running in the phase for regenerating a saturated molecular sieve feed stock.

In the case in which, as recalled above, the process is performed for the regeneration of the sieve feed stock at a heating temperature of between 200 and 300° C. (in the presence of a stream of inert gas), degradation of the water-saturation capacity of the molecular sieve feed stock is observed. Such a degradation would lead to stoppage of the industrial plant, in order to renew the sieve feed stock, under conditions which are incompatible with the running of an industrial drying plant.

Besides the molecular sieve, the composition sed in the process according to the invention comprises additives which are generally used in this field, in particular a clay-based binder which allows the shaped zeolite products to retain their ability to be shaped and their strength. The composition is generally in the form of pearls, or granules. With regard to their strength and their effective desiccating power, it is desirable for the granules to be essentially cylinder-shaped, to have a diameter of from 0.5 to 5 mm and a length of from 3 to 15 mm, and for the pearl have a diameter of from 1 to 5 mm.

EXAMPLES

The examples which follow are given purely for the purpose of non-limiting illustration of the process according to the invention.

Example 1

Drying of a Stream of F32 with a Feed Stock of 3A Type Molecular Sieve

A feed stock of 40.8 g of Ceca NK 30 (3 Å) sieves, in the form of granules with a diameter in the region of 1.5 mm and a length of between 5 and 10 mm, is placed inside a stainless steel drying tube (6), with an inside diameter of 14 mm and a height of 750 mm. The drier thus has a working height of about 380 mm, and it is equipped with a jacket for heating the sieve feed stock.

The feed stock preactivation treatment is carried out by heating to 200° C.

A stream of F32 gas containing 4100 ppm of water is then circulated through this drying tube at a flow rate of 44 l/h, at a temperature of about 20° C. and at a pressure of 1 atm, and the efficacy of the drying is monitored by measuring the water content, this being carried out using an electrical conductivity cell (7) coupled to a conductimeter (8) which is itself connected to a recorder (9) and an automatic stopping device (10).

The dry gas then passes through a buffer reservoir with a volume of 5 liters (15), from which it is sent, with the aid of a membrane pump (1) to a humidifier composed of a column of glass beads (3) and a plunger (4) which introduces liquid water into the system at a flow rate of 0.4 ml/h, such that the stream of dried F32 is again humidified to the abovementioned value of 4100 ppm of water. After this humidification and passage into a homogenization tank (5), the stream returns to the drier (6).

A 10-liter buffer tank (11) allows the pressure of the stream of F32 gas to be maintained at a value in the region of 1 atm.

The assembly described in FIG. 1 thus constitutes a gas-phase drying loop which simulates the running of a drying column for continuously treating a stream of wet F32 gas.

A water content for the F32 of less than 10 ppm is measured at the drying tube outlet.

The deviation from the output signal of the cell, indicating that the water-saturation capacity of the sieve feed stock has been reached, occurs after running for 18 h 30, which corresponds to a water-saturation capacity of 19.9% relative to the weight of dry sieve.

Example 2

Regeneration of the Feed Stock of 3A Type Molecular Sieve by Heating at 200° C. and at a Pressure of 1 mm Hg:

The assembly described in FIG. 1 also makes it possible to carry out several cycles for the same molecular sieve feed stock; each cycle comprises the continuous drying of wet F32 to the point of water-saturation of the sieve feed stock, followed by regeneration of the said feed stock. These cycles are carried out with a minimum consumption of F32.

After running for 18 h 30 and reaching the water-saturation capacity of the sieve feed stock as described in Example 1, circulation of the stream of wet F32 gas is stopped by closing the appropriate valves.

A stream of helium is then circulated, for 2 hours at room temperature, in the drying tube (6), the aim of A, this operation being to remove the F32 remaining between the granules of the molecular sieve feed stock. An auxiliary dryer (16) may be connected as shown in FIG. 1.

Valves (18) and (19) are thus closed and valve (22) is opened, so as to connect the drying tube (6) to a vacuum pump, via a metal trap immersed in liquid nitrogen.

The pressure in the said tube is thus lowered to a value of 1 mm Hg. The temperature in the drying tube (6) is set at 200° C. by circulating a heat-conducting fluid in the jacket of the said drier.

These temperature and pressure conditions are maintained for about 2 hours, until complete desorption of the water and of the small amount of F32 still adsorbed in the sieve feed stock. The water (and the F32) thus desorbed are retained in the liquid nitrogen trap, the weight of which is determined at regular time intervals. The regeneration treatment is stopped when the weight of the trap is more or less constant.

The drying test as defined in Example 1 is then repeated with the sieve feed stock thus regenerated.

The water-saturation capacity of the sieve feed stock is reached after running for 19 hours. It is 18.4%, and thus represents 92.5% of the water-saturation capacity determined at the end of Example 1.

This example thus shows that the water-saturation capacity is maintained at a more or less constant value after the regeneration treatment, which is advantageously included in the process for drying wet F32 according to the invention.

Example 3

Regeneration of a Feed Stock of 3A Type Molecular Sieves with a Stream of Helium, Carried Out with 3 Steady Temperature Regimes:

Example 1 is repeated with a fresh feed stock of 41.1 g of Ceca NK 30 (3 Å) molecular sieves.

The saturation capacity is reached after running for 19 hours. It is 18.5% relative to the weight of dry sieves.

The sieve feed stock is then regenerated by circulating a stream of helium in the drying tube (6), at normal atmospheric pressure and under the following conditions:

at 120° C. for 2 hours, then at 150° C. for 1 hour 30, then at 200° C. for 2 hours.

Chromatographic monitoring (14) of the desorbed F32 shows that the corresponding amounts of F32 (expressed relative to the initial amount of F32 adsorbed) are about 70% after the steady regime at 120° C. and about 90% after the steady regime at 150° C.

Chromatographic monitoring (14) of the water in the stream of He shows that, after the steady regime at 200° C., more than 95% of the water adsorbed onto the sieve feed stock has been desorbed.

The drying test as defined in Example 1 is then repeated with the sieve feed stock thus regenerated.

A water-saturation capacity of 16.9% is measured. Such a value corresponds to 91.3% of the water-saturation capacity achieved at the end of the drying step of the present example.

This example thus shows that the water-saturation capacity is maintained at a more or less constant value after the regeneration treatment, which is advantageously included in the process for drying wet F32 according to the invention.

Example 4

40.3 g of a sieve feed stock which is not fresh are used, the water-saturation capacity of these sieves, determined previously according to Example 1, being 14.2%.

A series of drying/regeneration cycles is carried out using this sieve feed stock; each cycle comprises the continuous drying of the wet F32, carried out in accordance with Example 1 to the point of water-saturation of the feed stock, and followed by regeneration of the said feed stock in accordance with the following temperature profile:

3 hours at 120°

3 hours at 160°

2 hours at 200°.

It is found that 98% of the initial amount of F32 adsorbed is desorbed after 3 hours at 160° C.

The results are collated in the following table. They show that the water-saturation capacity of the sieve feed stock is kept more or less constant.

| Cycle No. | Water capacity (%) |
|---|---|
| 1 | 14.2 |
| 2 | 14.3 |
| 3 | 14.5 |
| 4 | 13.0 |
| 5 | 15.3 |

Comparative Example

Example 1 is repeated with a fresh feed stock of 40.8 g of sieves.

The water-saturation capacity is reached after running for 19 h. It is 18.4% relative to the weight of dry sieves.

The regeneration is carried out while flushing with dried helium (12) preheated to 150° C. (oven 13), the bed of sieves being simultaneously heated via the drier (6) jacket; the aim of these methods is to very rapidly reach a temperature of 200° C. on all of the sieve feed stock, as occurs in practice in an industrial process.

After a steady regime of 2 hours at this temperature of 200° C., the sieve is cooled and 35.3 g of this feed stock are subjected to the drying test as defined in Example 1.

The water-saturation capacity of the sieve feed stock is reached, in this case, after running for 10 hours and is only 11.2%. This value corresponds to a 40% decrease relative to the initial saturation capacity, before regeneration.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated.

What is claimed is:

1. A process for drying wet F32, which comprises placing a stream of the said F32 in continuous contact with a food stock of a composition comprising a molecular sieve selected from a 3A, 4A or 5A type sieve, at a first temperature of between 5 and 78° C. and at a first pressure of between 0.6 and 25 atm, wherein she sieve feed stock is regenerated by the process which consists in passing a stream of an inert gas over the feed stock, at a second pressure at about atmospheric pressure:

(i) at a second temperature between 70° C. and 170° C., for the time required to remove at least 80%, of the initial amount of F32 absorbed in the feed stock, and then (ii) at a third temperature between 180° C. and 300° C., for the time required to remove at least 90%, of the initial amount of water absorbed in the feed stock.

2. The process according to claim 1, wherein the stream of F32 to be dried is a stream of gas, and the first pressure is between 0.6 and 10 atm.

3. The process according to claim 2, wherein the first pressure is between 0.8 and 5 atm.

4. The process according to claim 1, wherein the stream of F32 comprises a water content of less than 10,000 ppm.

5. The process according to claim 4, wherein the water content is less than 6000 ppm.

6. The process according to claim 1, wherein the wet F32 is placed in contact with the sieve feed stock in a column located downstream of a plant for manufacturing F32.

7. The process according to claim 1, wherein the molecular sieve used as a 3A type sieve.

8. The process according to claim 1, wherein the first temperature is room temperature.

9. The process according to claim 1, wherein the first pressure is between 0.8 and 17 atm.

10. The process according to claim 1, wherein the second temperature is between 80° C. and 165° C. and at least 90% of the initial amount of F32 absorbed in the feed stock is removed.

11. The process according to claim 1, wherein the third temperature is between 190° C. and 250° C. and at least 95% of the initial amount of F32 absorbed in the feed stock is removed.

12. The process according to claim 1, wherein the inert gas is helium.

13. A process for drying wet F32, which comprises placing a stream of the said F32, comprising a water content of less than 10,000 ppm, in continuous contact with a feed stock of a composition comprising a molecular sieve selected from a 3A, 4A or 5A type sieve, at a temperature of between 5 and 78° C., and at a pressure of between 0.6 and 25 atm, wherein the sieve feed stock is regenerated by the process which consists in passing a stream of an inert gas over the feed stock, at a pressure at about atmospheric pressure:
(i) at a temperature between 70° C. and 170° C., for the time required to remove at least 80%, of the initial amount of F32 absorbed in the feed stock, and then
(ii) at another temperature between 180° C. and 300° C., for the time required to remove at least 90%, of the initial amount of water absorbed in the feed stock.

* * * * *